United States Patent [19]
O'Neil

[11] Patent Number: 6,056,727
[45] Date of Patent: *May 2, 2000

[54] APPARATUS FOR PATIENT-CONTROLLED INFUSION

[76] Inventor: Alexander George Brian O'Neil, 200 Churchill Avenue, Subiaco, Australia, WA 6008 AU

[ * ] Notice: This patent issued on a continued prosecution application filed under 37 CFR 1.53(d), and is subject to the twenty year patent term provisions of 35 U.S.C. 154(a)(2).

[21] Appl. No.: 08/610,803

[22] Filed: Mar. 7, 1996

Related U.S. Application Data

[63] Continuation of application No. 08/170,266, filed as application No. PCT/GB92/01184, Jun. 30, 1992, abandoned.

[30] Foreign Application Priority Data

Jul. 1, 1991 [AU] Australia ................................ PK6940
May 25, 1992 [AU] Australia ................................ PL2573

[51] Int. Cl.$^7$ .................................................. A61M 5/178
[52] U.S. Cl. ........................... 604/183; 604/133; 604/246
[58] Field of Search .................................. 604/183–186, 604/190, 216–217, 246, 252, 257, 262, 323–325, 142, 153, 38, 407, 408, 133–136

[56] References Cited

U.S. PATENT DOCUMENTS

| | | | |
|---|---|---|---|
| 1,517,849 | 12/1924 | McLellan | 604/186 X |
| 2,156,023 | 4/1939 | McKay | 604/184 |
| 2,645,224 | 7/1953 | Beebe . | |
| 2,923,293 | 2/1960 | Nawoj et al. | 604/407 X |
| 3,952,919 | 4/1976 | Hansen et al. | 604/183 X |
| 4,147,280 | 4/1979 | Spatz . | |
| 4,187,847 | 2/1980 | Loeser . | |
| 4,210,173 | 7/1980 | Choksi et al. | 604/186 X |
| 4,298,000 | 11/1981 | Thill et al. . | |
| 4,424,056 | 1/1984 | Urquhart et al. | 604/56 |
| 4,828,551 | 5/1989 | Gertler et al. . | |
| 4,838,855 | 6/1989 | Lynn | 604/49 |
| 4,904,243 | 2/1990 | Bruera . | |
| 5,059,173 | 10/1991 | Sacco | 604/80 |
| 5,135,491 | 8/1992 | Baldwin | 607/53 |
| 5,207,661 | 5/1993 | Repschlager | 604/317 |

FOREIGN PATENT DOCUMENTS

| | | |
|---|---|---|
| 0 289 856 | 11/1988 | European Pat. Off. . |
| 0 342 651 | 11/1989 | European Pat. Off. . |
| 0392566 | 10/1990 | European Pat. Off. . |
| 2588757 | 4/1987 | France . |
| 348454 | 5/1931 | United Kingdom . |
| 2 084 263 | 4/1982 | United Kingdom . |
| 8700758 | 2/1987 | WIPO . |
| 9108002 | 6/1991 | WIPO . |
| WO 91/14468 | 10/1991 | WIPO . |

*Primary Examiner*—Michael Powell Buiz
*Assistant Examiner*—A. T. Nguyen
*Attorney, Agent, or Firm*—Ratner & Prestia

[57] ABSTRACT

A reservoir is connected to a manually operable pump such as an aspirating syringe via a flow control tube which has a fine bore of accurately known size. Actuation of the syringe by the patient discharges a fixed volume of drug via a non-return valve to the patient. The syringe is refilled by a return spring drawing liquid from the reservoir at a rate controlled by the bore of the flow control tube, thus setting a maximum dosage rate.

13 Claims, 5 Drawing Sheets

APPARATUS FOR PATIENT-CONTROLLED INFUSION

This application is a continuation of application Ser. No. 08/170,266 filed Aug. 23, 1994, abandoned, which is a national stage of PCT/GB92/01184 filed Jun. 30, 1992.

This invention relates to an improved apparatus for effecting patient-controlled infusion of liquid medicaments and is particularly, but not exclusively, applicable to patient-controlled analgesia (PCA).

It has been recognised for some time that PCA is desirable in many situations of chronic or temporary (for example, post operative) pain. Before the advent of PCA, analgesia relied on periodic injections of drugs such as synthetic opioids by the physician or nurse, typically at 4-hour intervals. This has the disadvantage that for most of the time the patient's analgesic level is significantly above or below the optimum.

PCA improves on that prior art by enabling the infusion of small quantities of analgesics at regular intervals as perceived to be required by the patient. However, to date PCA has been effected by sophisticated electronic pump systems which have a number of disadvantages:

(a) They are expensive.

b) They are complex and require skilled maintenance.

(c) They are capable of administering an overdose as a result of machine failure or of operator error in setting up; a number of deaths from this cause have been reported.

An object of the present invention is to provide an improved PCA apparatus which is simple and inexpensive to manufacture and use, and which has a high level of inherent safety.

The present invention accordingly provides apparatus for patient-controlled infusion of a liquid medicament, the apparatus comprising a reservoir for the medicament, a positive displacement pump having a predetermined working volume, a first conduit connecting the reservoir to the pump, a second conduit extending from the pump and having a distal end to be inserted in the patient, and a one-way valve in the second conduit permitting liquid flow from the pump to the patient and preventing reverse flow; the pump being manually operable to displace liquid through the valve and comprising resilient restoring means for returning the pump to its initial state while drawing liquid from the reservoir through the first conduit; and in which the first conduit has a restricted flow rate chosen in conjunction with the working volume of the pump to define a predetermined maximum dosage rate.

An important preferred feature of the invention resides in the provision of means for introducing a priming liquid into the second conduit without the priming liquid passing through the first conduit, which means may conveniently comprise a dismountable connection between the pump and the second conduit whereby the pump may be removed to allow the second conduit to be filled with priming liquid through said connection.

Preferably the pump is a syringe having a plunger biased outwardly by resilient means.

The second conduit preferably includes means for venting gas therefrom, suitably in the form of a filter which is also capable of removing bacteria.

In one form of the invention, means are provided for introducing liquid into the reservoir while the apparatus is in use, preferably in the form of a third conduit extending from the reservoir and terminating in an injection port.

The third conduit preferably includes a one-way valve, and may include an air-trapping filter or alternatively a branch for removing air.

For safety reasons, the injection port and/or the air removing branch if present may be provided with lockable covers.

The reservoir may suitably comprise a piston and cylinder or a flexible bag.

Embodiments of the invention will now be described, by way of example only, with reference to the drawings in which.

Figure 1:
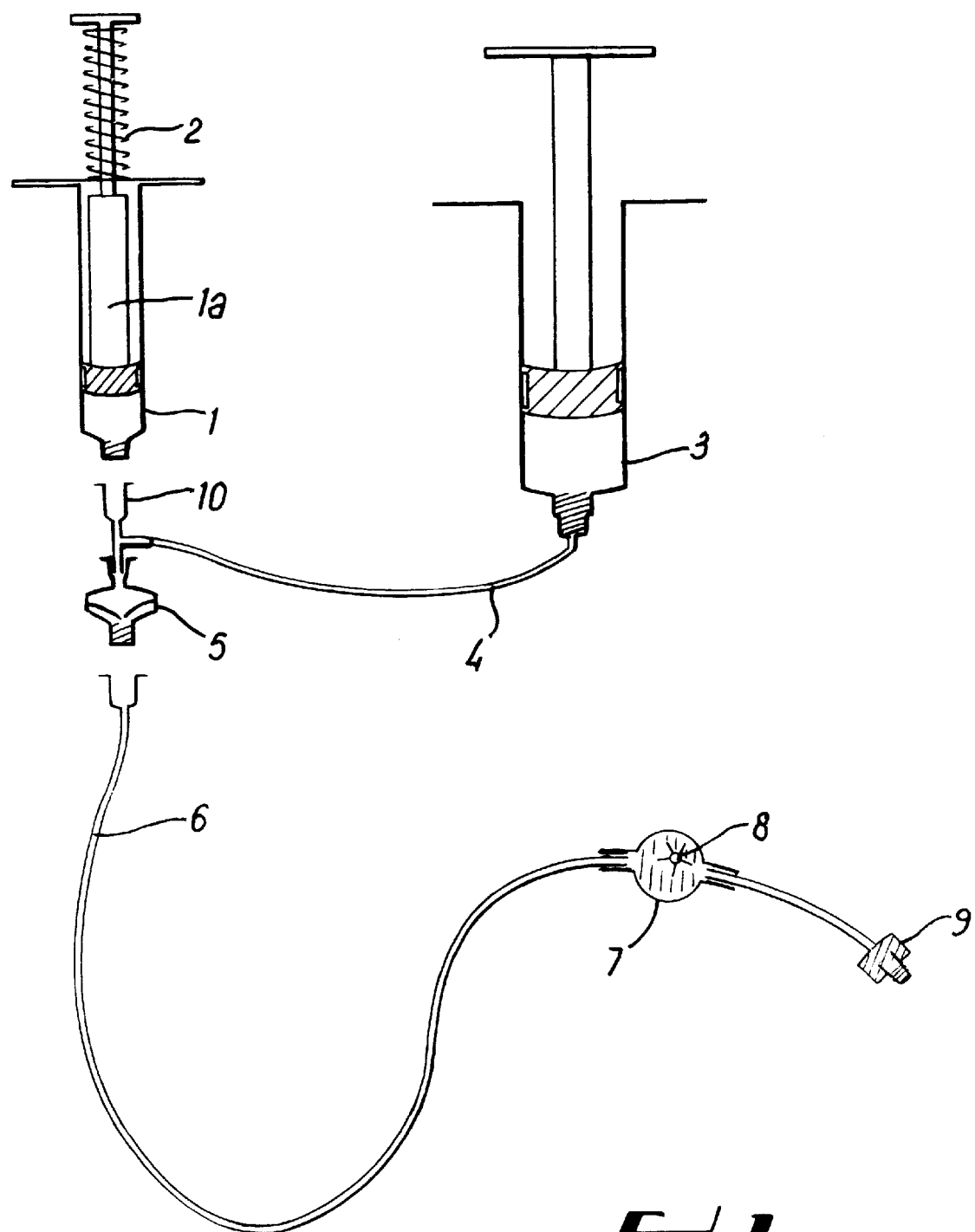
FIG. 1 is a schematic view of a PCA apparatus forming a first embodiment of the invention.

Referring to FIG. 1, the apparatus comprises a reservoir in the form of a syringe 3 which is in communication via a small bore tube 4 with a metering device in the form of an aspirating syringe 1 whose plunger 1a is biased upwardly by a return spring 2. The aspirating syringe 1 is arranged to discharge via a patient line comprising a one-way valve 5, tubing 6 and male luer lock connection 9 to an intravenous catheter secured to the patient. Interposed in the tubing 6 is a filter 7 of known type for preventing passage of bacteria and including a hydrophilic membrane 8 which discharges to atmosphere any air which inadvertently enters the system. The aspirating syringe 1 can be connected to and disconnected from the patient line by means of a connection joint 10.

In use, the reservoir 3 is filled with a quantity of analgesic suitable for pain control over a period, for example 4 hours. Once the system is primed with liquid and connected to the patient, depression of the plunger 1a causes a quantity of analgesic equal to the volume of the aspirating syringe 1, typically about 0.5 ml, to be infused. When the plunger 1a is released, it returns under the influence of the spring 2, but at a rate which is determined by the rate of flow of liquid from the reservoir 3 through the small bore tube 4. The overall infusion rate is thus controlled by suitable selection of the volume of the aspirating syringe 1 and the flow-resistance of the tube 4 in relation to a given liquid.

The tube 4 is preferably a plastics tube having a very narrow bore and a relatively thick wall, the latter ensuring that it does not kink in use. Such a tube and the method of producing it are described in published International Patent Application W088/02637. The tube 4 preferably has a length in the range 1 to 40 cm and a lumen diameter in the range 0.001 inch (0.025 mm) to 0.008 inch (0.20 mm). In a particularly preferred form, the lumen diameter is 0.070 mm and the tube length 23 mm.

The use of fine bore tubing not only sets the refill time of the aspirating syringe 1, but also acts as a safety factor in inhibiting siphoning of liquid from the reservoir 3 to the patient. As an additional safety factor, the one-way valve 5 should have an opening pressure greater than the maximum possible hydrostatic pressure which could be present by elevating the reservoir above the patient to the maximum height permitted by the length of the tubing.

Figure 2:
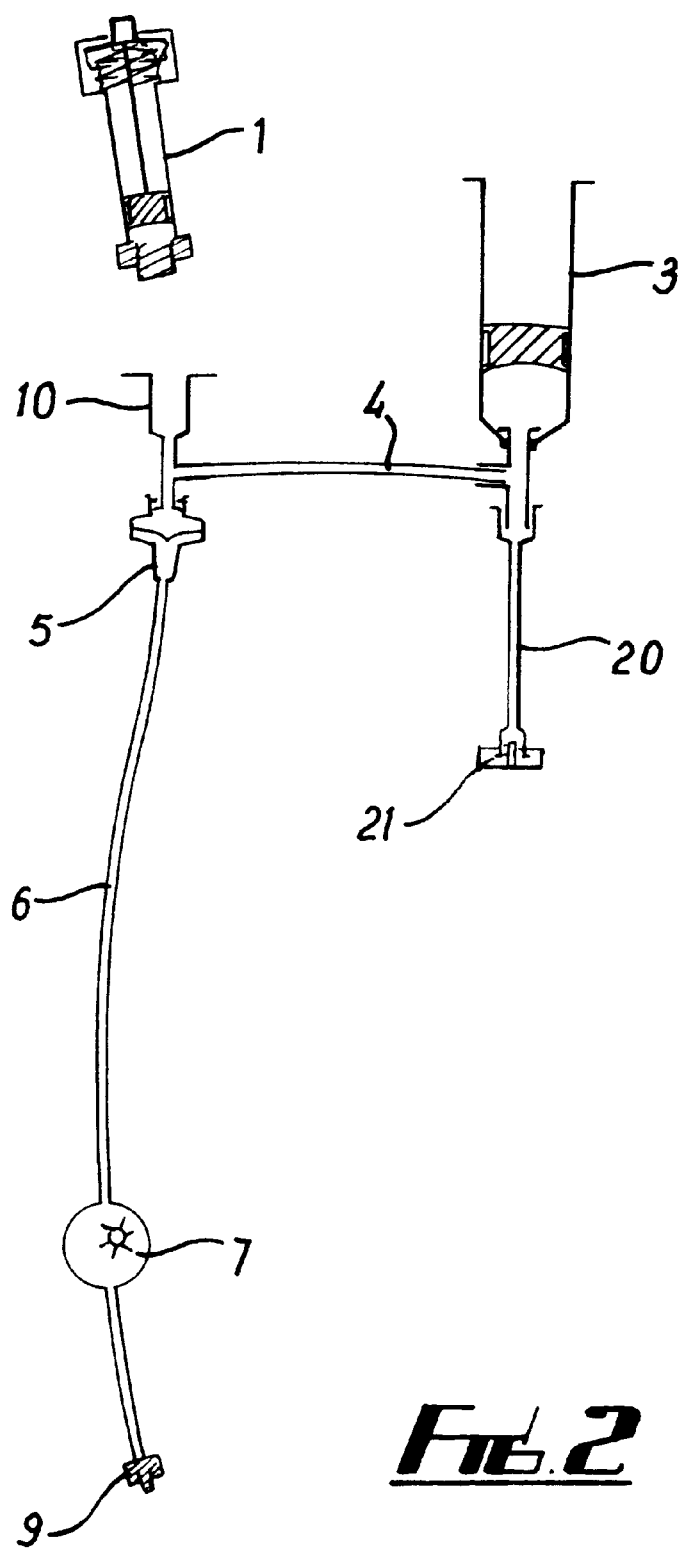
FIG. 2 is a schematic view of a second embodiment containing additional features.

The embodiment of FIG. 2 is similar to that of FIG. 1 and like parts are denoted by like reference numerals. In this embodiment, the reservoir 3 is provided with a fill line 20 terminating in an injection site 21 where the system can be filled or emptied by means of a standard hypodermic syringe.

Figure 3:
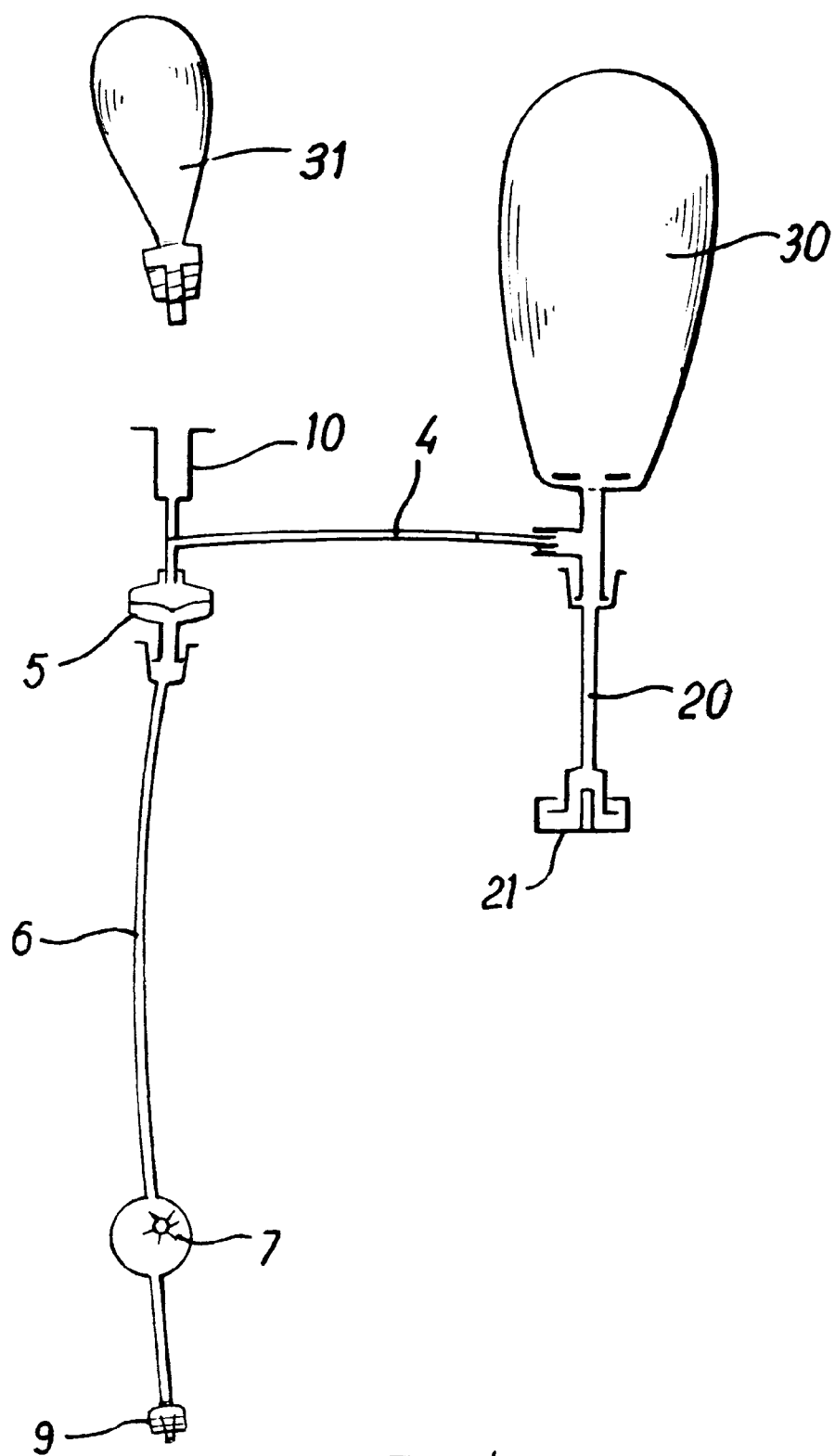
FIG. 3 is a similar view of a third embodiment being a modified version of the embodiment of FIG. 2.

The embodiment of FIG. 3 is similar to that of FIG. 2, but the reservoir is in the form of a collapsible bag 30, and the aspirating syringe is replaced by a balloon 31. The balloon 31 is a thick-walled rubber balloon with sufficient recovery force to draw liquid from the reservoir 30 through the small bore tube 4.

Figure 4:
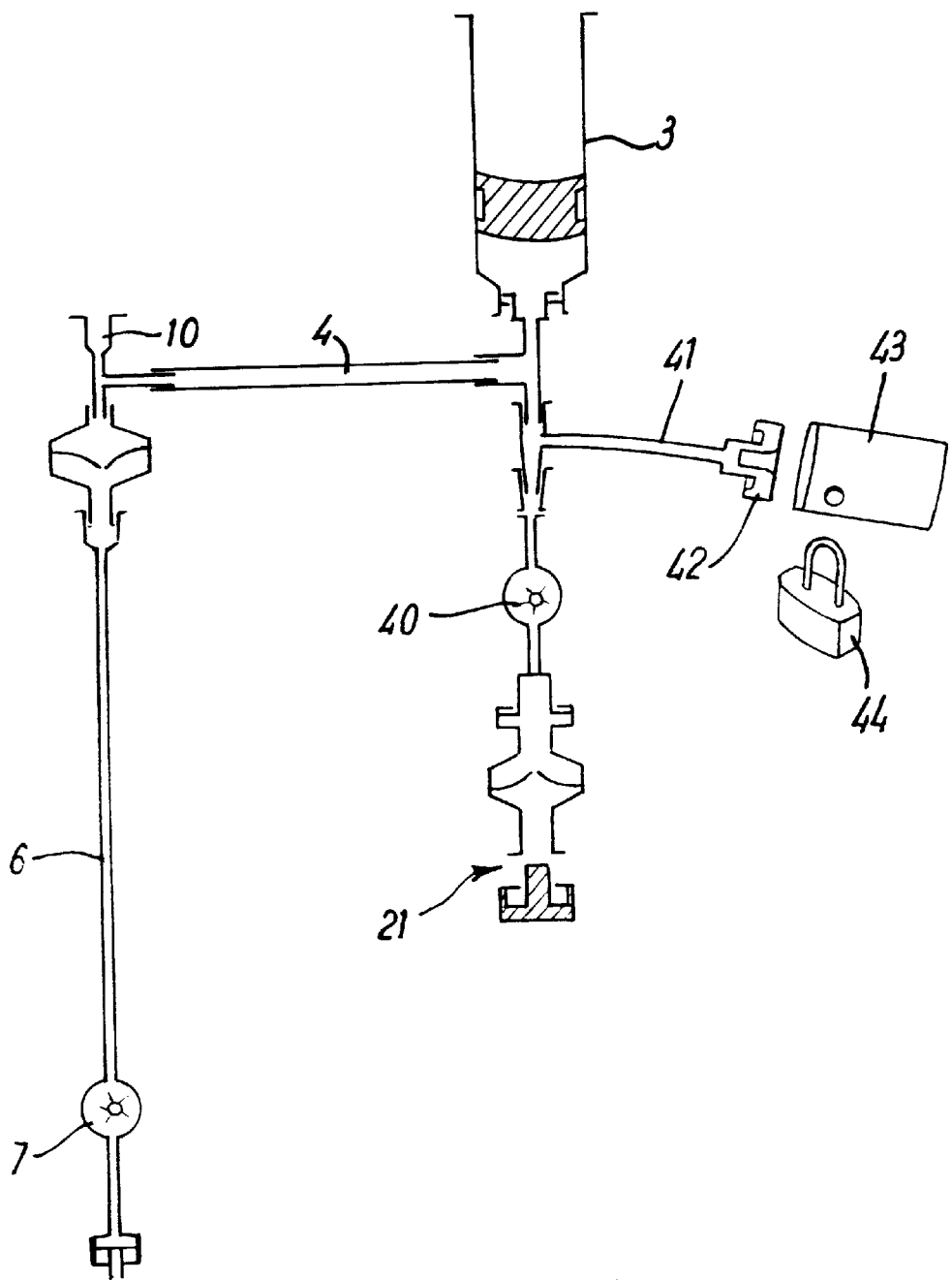
FIG. 4 is a similar view of a further modified embodiment.

FIG. 4 shows optional features which may be added to the systems of FIGS. 2 and 3. A gas-trapping filter 40 may be included in the fill line 20 to prevent any air inadvertently introduced at the injection site 21 from reaching the reservoir 3. Alternatively a branch 41 may be provided, ending in a port 42 for removing from the system air either introduced inadvertently or at the initial purging of the system. A one-way valve 45 may be included in the fill line 20 to prevent removal of liquid from the system.

A cover 43 may be placed over the port 42 and secured in place by a padlock 44 to prevent accidental or unauthorised use. The cover 43 and padlock 44 may similarly be used to bar unatithorised access to the injection site 21.

Figure 5:
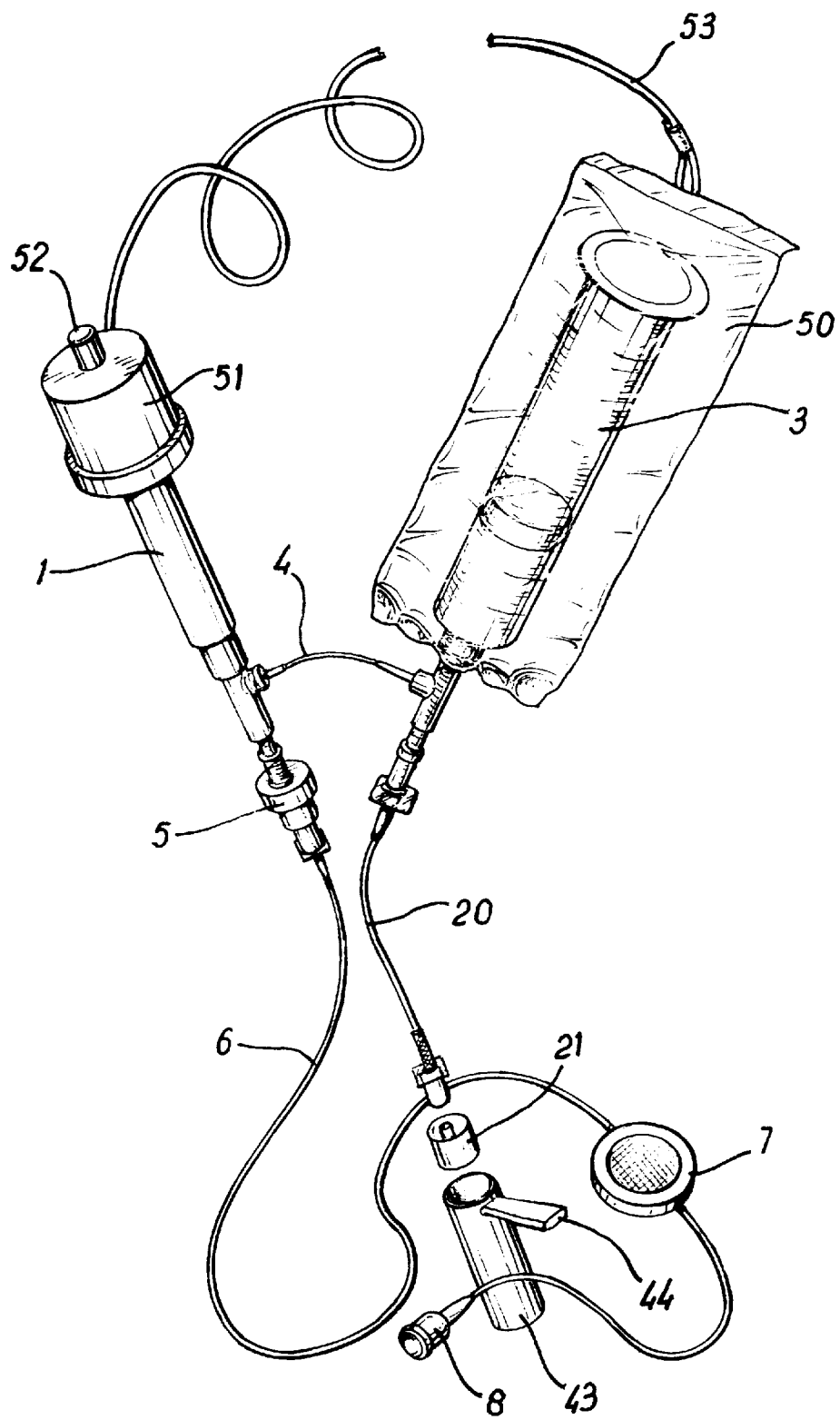
FIG. 5 is a perspective view of a practical embodiment suitable for ambulatory use.

FIG. 5 illustrates one presently preferred, practical implementation of the invention. Again, like parts are denoted by like reference numerals. In FIG. 5, the reservoir syringe 3 is enclosed within a transparent plastics bag 50 for reasons of safety and hygiene. The return spring of the aspirating syringe 1 is housed within a cylindrical casing 51, the plunger being actuated by a patient demand button 52 extending from the casing 51. The syringe 1 and the bag 50 are linked by a cord 53 which allows the apparatus to be hung around the patient's neck for ambulatory use.

An important preferred feature is the ability to remove the syringe 1 (or equivalent) to assist in priming the system. The tube 4 has such an extremely fine bore that it is difficult to force liquid through it from the reservoir 3 to prime the system, and such a procedure would take an extremely long time. Accordingly, to prime the system the aspiration syringe 1 is removed from the connector 10 and the patient line is filled with liquid, which may be done by connecting a relatively large syringe at the connector 10 and injecting from this to overcome the resistance of the one-way valve 5. In the case of the embodiments of FIGS. 2 to 5, the reservoir fill line is also primed with liquid at this stage.

The aspirating syringe 1 is then re-applied to the connector 10 with its plunger 1a held down. On release of the plunger 1a, fluid is drawn through the fine bore tube 4. This fluid is initially air which becomes trapped in the syringe 1, but the volume of air involved (equal to the internal volume of the tube 4) is so small that it does not affect the operation of the system.

The invention thus provides a patient-controlled apparatus which is of simple and inexpensive construction and has a high level of inherent safety. The apparatus is extremely simple to operate. Owing to its simplicity and cheapness it can be used as a disposable item. The apparatus can be manufactured for use with a particular medicament by suitable choice of aspirating syringe and bore of the flow control tube; on-site adjustment is then not required, and the apparatus can be used by nursing staff without specialist training who simply have to recharge the reservoir from time to time, suitably by injecting a single standard 4-hour bolus into the reservoir.

Although described with particular reference to patient-controlled analgesia, the invention can be applied to patient-controlled infusion of other medicaments such as sedatives and antiemetics.

I claim:

1. Apparatus for patient-controlled infusion of a liquid medicament, the apparatus comprising a reservoir for the medicament, a positive displacement pump having a predetermined working volume, a first conduit connecting the reservoir to the pump, a second conduit connected to and extending from the pump and having a distal end to be inserted in the patient, a one-way valve positioned between the pump and the distal end of the second conduit permitting liquid flow from the pump to the patient and preventing reverse flow, and a dismountable connection means wherein the second conduit being connected to the pump by said dismountable connection means for introducing a priming liquid into the second conduit without the priming liquid passing through the first conduit; the pump being manually operable to displace liquid through the valve and comprising resilient restoring means for returning the pump to its initial state while drawing liquid from the reservoir through the first conduit; and in which the first conduit is a capillary tube and has a length in the range 1 cm to 40 cm and a lumen diameter in the range of 0.025 mm to 0.20 mm whereby the flow rate of liquid medicament through the first conduit is restricted to a rate chosen in conjunction with the working volume of the pump to define a predetermined maximum dosage rate; and wherein the length and the lumen diameter of the first conduit are chosen so as to define a small internal volume which does not affect the operation of the system.

2. Apparatus according to claim 1, in which the reservoir comprises a piston and cylinder.

3. Apparatus according to claim 1, in which the reservoir comprises a resilient bag.

4. Apparatus according to claim 1, in which the pump is a syringe having a plunger biased outwardly by resilient means.

5. Apparatus according to claim 1, in which the second conduit includes means for venting gas from the second conduit.

6. Apparatus according to claim 5, in which the venting means comprises a filter which is also capable of removing bacteria.

7. Apparatus according to claim 1, further including means defining an aperture in the reservoir for introducing liquid into the reservoir while the apparatus is in use.

8. Apparatus according to claim 7, in which said introducing means comprises a third conduit extending from the reservoir and terminating in an injection port.

9. Apparatus according to claim 8, in which the third conduit includes a one-way valve.

10. Apparatus according to claim 8, in which the third conduit includes an air trapping filter.

11. Apparatus according to claim 8, in which the third conduit is provided with a branch for removing air.

12. Apparatus according to claim 8, in which the injection port is provided with a lockable cover.

13. Apparatus according to claim 1, wherein the first conduit has a lumen diameter of 0.070 mm and a length of 23 mm.

* * * * *